(12) United States Patent
Khoury

(10) Patent No.: US 8,728,011 B2
(45) Date of Patent: May 20, 2014

(54) MULTI WIRE SHEATH

(76) Inventor: Michael D. Khoury, St. George, UT (US)

(*) Notice: Subject to any disclaimer, the term of this patent is extended or adjusted under 35 U.S.C. 154(b) by 36 days.

(21) Appl. No.: 13/549,465

(22) Filed: Jul. 14, 2012

(65) Prior Publication Data
US 2013/0041350 A1 Feb. 14, 2013

Related U.S. Application Data

(60) Provisional application No. 61/510,786, filed on Jul. 22, 2011.

(51) Int. Cl.
*A61M 25/00* (2006.01)

(52) U.S. Cl.
USPC .................................................. 600/585

(58) Field of Classification Search
USPC ................. 600/433, 434, 585; 604/164.13
See application file for complete search history.

(56) References Cited

U.S. PATENT DOCUMENTS

| | | | |
|---|---|---|---|
| 4,988,356 A | 1/1991 | Crittenden et al. | |
| 5,203,772 A | 4/1993 | Hammerslag et al. | |
| 5,308,324 A | 5/1994 | Hammerslag et al. | |
| 5,372,587 A | 12/1994 | Hammerslag et al. | |
| 5,404,886 A | 4/1995 | Vance | |
| 5,480,382 A | 1/1996 | Hammerslag et al. | |
| 5,511,559 A | 4/1996 | Vance | |
| 5,573,520 A | 11/1996 | Schwartz et al. | |
| 5,653,759 A | 8/1997 | Hogan et al. | |
| 5,741,429 A | 4/1998 | Donadio, III et al. | |
| 5,830,156 A | 11/1998 | Ali | |
| 5,971,949 A | 10/1999 | Levin et al. | |
| 6,027,863 A | 2/2000 | Donadio, III | |
| 6,107,004 A | 8/2000 | Donadio, III | |
| 6,241,703 B1 | 6/2001 | Levin et al. | |
| 6,387,060 B1 | 5/2002 | Jalisi | |
| 6,679,853 B1 | 1/2004 | Jalisi | |
| 6,748,953 B2 | 6/2004 | Sherry et al. | |
| 7,137,991 B2 | 11/2006 | Fedie | |
| 7,179,269 B2 | 2/2007 | Welch et al. | |
| 7,296,333 B2 | 11/2007 | Jalisi | |
| 7,384,411 B1 | 6/2008 | Condado | |
| 7,402,141 B2 | 7/2008 | Heuser | |
| 7,637,924 B2 | 12/2009 | Gifford, III et al. | |
| 7,645,273 B2 | 1/2010 | Lualdi | |
| 7,699,800 B2 | 4/2010 | Dextradeur et al. | |
| 7,905,003 B2 | 3/2011 | Jalisi | |
| 7,922,710 B2 * | 4/2011 | Eidenschink et al. | 604/539 |
| 2002/0007152 A1 * | 1/2002 | Hermann et al. | 604/167.04 |

(Continued)

*Primary Examiner* — Max Hindenburg
*Assistant Examiner* — Jonathan M Foreman
(74) *Attorney, Agent, or Firm* — Blue Filament Law PLLC; Avery N. Goldstein

(57) ABSTRACT

A multi-guidewire sheath (MGS) is provided for cases where simultaneous guidewire access to multiple target arteries is required. Embodiments of the MGS have multiple guidewires in a single sheath configured with a single lumen. The MGS incorporates an engagement system to independently secure the one or more guidewires within the sheath to maintain the separate positions of the guidewires. Embodiments of the MGS are configured with a taper from the desired intra-arterial portion (e.g., conventional French sizes) to a larger diameter for the portion of the sheath outside (distal) the vessel. The distal segment of the MGS has a larger diameter to accommodate the engagement system to secure the independent positions of multiple guidewires, and a hemostatic valve seal and slit mounted in a rotating hub. The engagement system has a series of wire-lock engagement points positioned along the circumference of the MGS.

13 Claims, 3 Drawing Sheets

(56) References Cited

U.S. PATENT DOCUMENTS

| | | |
|---|---|---|
| 2003/0153845 A1 | 8/2003 | Emken et al. |
| 2003/0216760 A1 | 11/2003 | Welch et al. |
| 2003/0229340 A1 | 12/2003 | Sherry et al. |
| 2004/0123915 A1 | 7/2004 | Jalisi |
| 2004/0167564 A1 | 8/2004 | Fedie |
| 2004/0193246 A1 | 9/2004 | Ferrera |
| 2004/0220473 A1 | 11/2004 | Lualdi |
| 2004/0267191 A1 | 12/2004 | Gifford, III et al. |
| 2005/0131460 A1 | 6/2005 | Gifford, III et al. |
| 2005/0228417 A1 | 10/2005 | Teitelbaum et al. |
| 2006/0047222 A1 | 3/2006 | Heuser |
| 2006/0074441 A1 | 4/2006 | McGuckin et al. |
| 2007/0021819 A1 | 1/2007 | Krolik et al. |
| 2007/0043435 A1 | 2/2007 | Seguin et al. |
| 2007/0100371 A1 | 5/2007 | Fedie |
| 2007/0150045 A1 | 6/2007 | Ferrera |
| 2007/0250001 A1 | 10/2007 | Hilaire et al. |
| 2008/0045881 A1 | 2/2008 | Teitelbaum et al. |
| 2008/0140189 A1 | 6/2008 | Nguyen et al. |
| 2008/0154153 A1 | 6/2008 | Heuser |
| 2008/0183036 A1 | 7/2008 | Saadat et al. |
| 2008/0228108 A1 | 9/2008 | Jalisi |
| 2009/0012429 A1 | 1/2009 | Heuser |
| 2009/0076357 A1 | 3/2009 | Purdy |
| 2009/0082609 A1 | 3/2009 | Condado |
| 2009/0125045 A1 | 5/2009 | Heuser |
| 2009/0131924 A1 | 5/2009 | Meyer et al. |
| 2009/0198172 A1 | 8/2009 | Garrison et al. |
| 2010/0049137 A1 | 2/2010 | Fischer, Jr. |
| 2010/0106238 A1 | 4/2010 | Hilaire et al. |
| 2010/0324397 A1 | 12/2010 | Purdy |
| 2011/0034986 A1 | 2/2011 | Chou et al. |
| 2011/0082483 A1 | 4/2011 | Diamant et al. |
| 2011/0130819 A1 | 6/2011 | Cragg et al. |
| 2011/0130820 A1 | 6/2011 | Cragg et al. |
| 2011/0130824 A1 | 6/2011 | Cragg et al. |
| 2011/0130825 A1 | 6/2011 | Cragg et al. |
| 2011/0130826 A1 | 6/2011 | Cragg et al. |
| 2012/0271236 A1* | 10/2012 | Bruszewski ............ 604/167.03 |

* cited by examiner

MULTI WIRE SHEATH

CROSS-REFERENCE TO RELATED APPLICATIONS

This application is a non-provisional application that claims priority benefit of U.S. Provisional Application Ser. No. 61/510,786, filed Jul. 22, 2011; the contents of which are hereby incorporated by reference.

FIELD OF THE INVENTION

The present invention in general relates to arterial sheaths and method for surgical deployment thereof, and in particular to a vascular sheath that provides multiple independent guide wires within a single lumen.

BACKGROUND OF THE INVENTION

An endovascular procedure is a surgical procedure in which a catheter or other interventional device containing medications or miniature instruments is inserted percutaneously into a blood vessel for the treatment of a vascular disease or condition. Examples of endovascular procedures may include the insertion of a catheter in an occluded or narrowed vessel so as to open the occlusion with a balloon, position a stent, position a pressure monitoring lead, stabilize a vascular aneurysm, or any other number of indications. In general, a guidewire is used to support advancement of a catheter or other interventional device in a target vessel to be treated, and the devices may be positioned in the desired location under fluoroscopy.

For example, a catheter may be introduced over a guidewire and appropriately positioned in a patient's occluded vessel with a relatively stiff guidewire to cross the occlusion and provide sufficient rigidity and support to the catheter. A balloon catheter may then be introduced over the guidewire and the balloon inflated to open the lesion and/or to place a stent at the site of the lesion.

In many instances lesions or stenosis are present at a bifurcation in a patient's vessel, thereby requiring separate catheters and guidewires to be inserted into branches of the bifurcation, necessitating the introduction of multiple catheters and guidewires. Furthermore, a physician may want to introduce multiple interventional devices to the vessel, or desires to introduce drugs to a particular vascular situs, requiring more than one guidewire to be inserted and left in place so that another catheter or device can be employed. Unfortunately, when multiple guidewires are employed, the guidewires can become crossed or entangled within a vessel. In addition, the introduction of multiple guide wires is time consuming and compounds the attendant risks to the patient associated with any catheterization procedure.

Thus, there exists a need for a system that provides for the quick, safe, and efficient deployment of multiple guidewires simultaneously so that multiple catheter-borne interventional devices may be introduced, interchangeably, over any one of the indwelling guidewires. Furthermore, it is advantageous to have a system that allows for the placement of multiple parallel guidewires while avoiding entanglement or entwining of the guidewires.

SUMMARY OF THE INVENTION

An inventive multi-guidewire sheath (MGS) is provided for cases where simultaneous guidewire access to multiple target vessels is required. Embodiments of the MGS have multiple guidewires in a single sheath configured with a single lumen. The MGS incorporates an engagement system to independently secure the one or more guidewires within the sheath to maintain the separate positions of the guidewires. Certain embodiments of the MGS are configured with a flair from the desired intra-vascular portion (e.g., conventional French sizes) to a larger diameter for the portion of the sheath outside (distal) the vessel. The distal segment of the MGS has a larger diameter in specific embodiments to accommodate the engagement system to secure the independent positions of multiple guidewires, and a hemostatic valve seal and slit mounted in a rotating hub. The engagement system has a series of wire-lock engagement points positioned along the circumference of the MGS.

In operation, the rotation of the hub at the distal end of the MGS allows the slit of the hemostatic valve seal to line up with a desired wire-lock of the engagement system to allow the guidewire to be positioned in and out of the wire-lock. When the locked guidewire is to be used in the main sheath lumen, the hub is rotated to line up the valve-slit with the guidewire in the wire-lock. The lock is opened releasing the guidewire which is then moved through the valve-slit to the center hub of the hemostatic valve and then used in a conventional manner in a target vessel. Following the usage of the unlocked guidewire, the guidewire is returned through the valve-slit to the wire-lock to be re-engaged. The wire-lock when closed secures the guidewire in place preventing it from being dislodged while the main lumen of the sheath is used with other guidewires. The hub is then amenable to be rotated to line up the valve-slit with another wire-lock to access a different guidewire for serving the same or different target vessel.

DETAILED DESCRIPTION OF THE PREFERRED EMBODIMENTS

Figure 1:
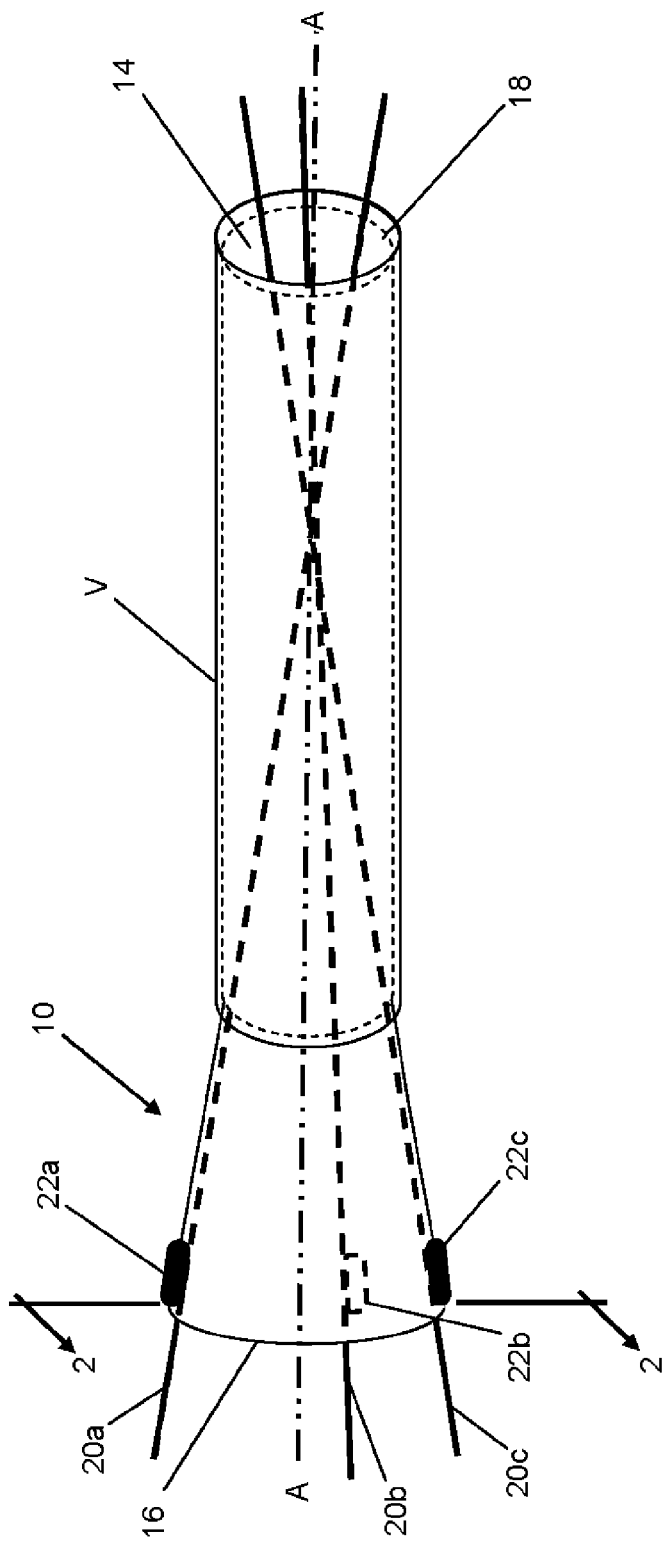
FIG. 1 is a perspective view of an inventive multi guidewire sheath (MGS) device.

An inventive multi-guidewire sheath (MGS) provides for the usage of multiple guidewires in a single sheath configured with a single lumen. A typical use of the MGS is cases where simultaneous guidewire access to multiple target arteries is required. The MGS incorporates an engagement system to independently secure the one or more guidewires within the sheath to maintain the separate positions of the guidewires. Embodiments of the MGS are configured with a taper from the desired intra-arterial portion (e.g., conventional French sizes) to a larger diameter for the portion of the sheath outside (distal) the vessel. The distal segment of the MGS has a larger diameter to accommodate the engagement system to secure the independent positions of multiple guidewires, and a hemostatic valve seal and slit mounted in a rotating hub. The engagement system has a series of wire-lock engagement points positioned along the circumference of the MGS. The MGS is readily constructed with biocompatible polyurethane or similar materials, with optional reinforcement with metal, or Nitinol present in these embodiments where additional rigidity are required. It is appreciated that an inventive sheath optionally and readily incorporates substances such as radio opaque marking compounds on the catheter for accurate positioning such as barium sulfate; slip agents for smooth artery entry such as hydrophilic gels sold under that tradename GLIDEX®; anticoagulants such as heparin; sustained release drugs such as antibiotics and plaque formation inhibitors; and combinations thereof.

Vessels that are readily repaired according to the present invention include arteries, veins, the aorta, and other anatomies such as cerebral meninges, cerebral ventricles, urinary tract structures and those that otherwise benefit from minimally invasive surgery. These structures are collectively defined herein as vessels or with the corresponding adjective "vascular".

A subject or patient that benefits from the present invention illustratively includes a variety of creatures including humans; and non-human mammals such as rodents, primates, cows, horses, dogs, cats, and sheep.

In operation, the rotation of the hub at the distal end of the MGS allows the slit of the hemostatic valve seal to line up with a desired wire-lock of the engagement system to allow the guidewire to be positioned in and out of the wire-lock. When the locked guidewire is to be used in the main sheath lumen, the hub is rotated to line up the valve-slit with the guidewire in the wire-lock. The lock is opened releasing the guidewire which is then moved through the valve-slit to the center hub of the hemostatic valve and then used in a conventional manner in a target vessel. Following the usage of the unlocked guidewire, the guidewire is returned through the valve-slit to the wire-lock to be reengaged. The wire-lock when closed secures the guidewire in place preventing it from being dislodged while the main lumen of the sheath is used with other guidewires. The hub is then amenable to be rotated to line up the valve-slit with another wire-lock to access a different guidewire for serving the same or different target vessel.

Referring now to FIGS. 1 and 2A-2D, an inventive multi-guidewire sheath (MGS) is depicted generally at 10. The MGS 10 includes a single inner lumen 14 for vascular access. The proximal portion 18 of the MGS 10 has a diameter to fit into a desired intra-vascular portion V. The distal segment 16 of the MGS 10 has a larger diameter to accommodate an engagement system (22a, 22b, 22c) to secure the independent positions of multiple guidewires (20a, 20b, 20c), and a hemostatic valve seal 26 and slit 28 mounted in a rotating hub 24. It is noted that in other embodiments of the MGS 10 there may be only two guidewires, or in other embodiments, more than three wires.

Figure 2:
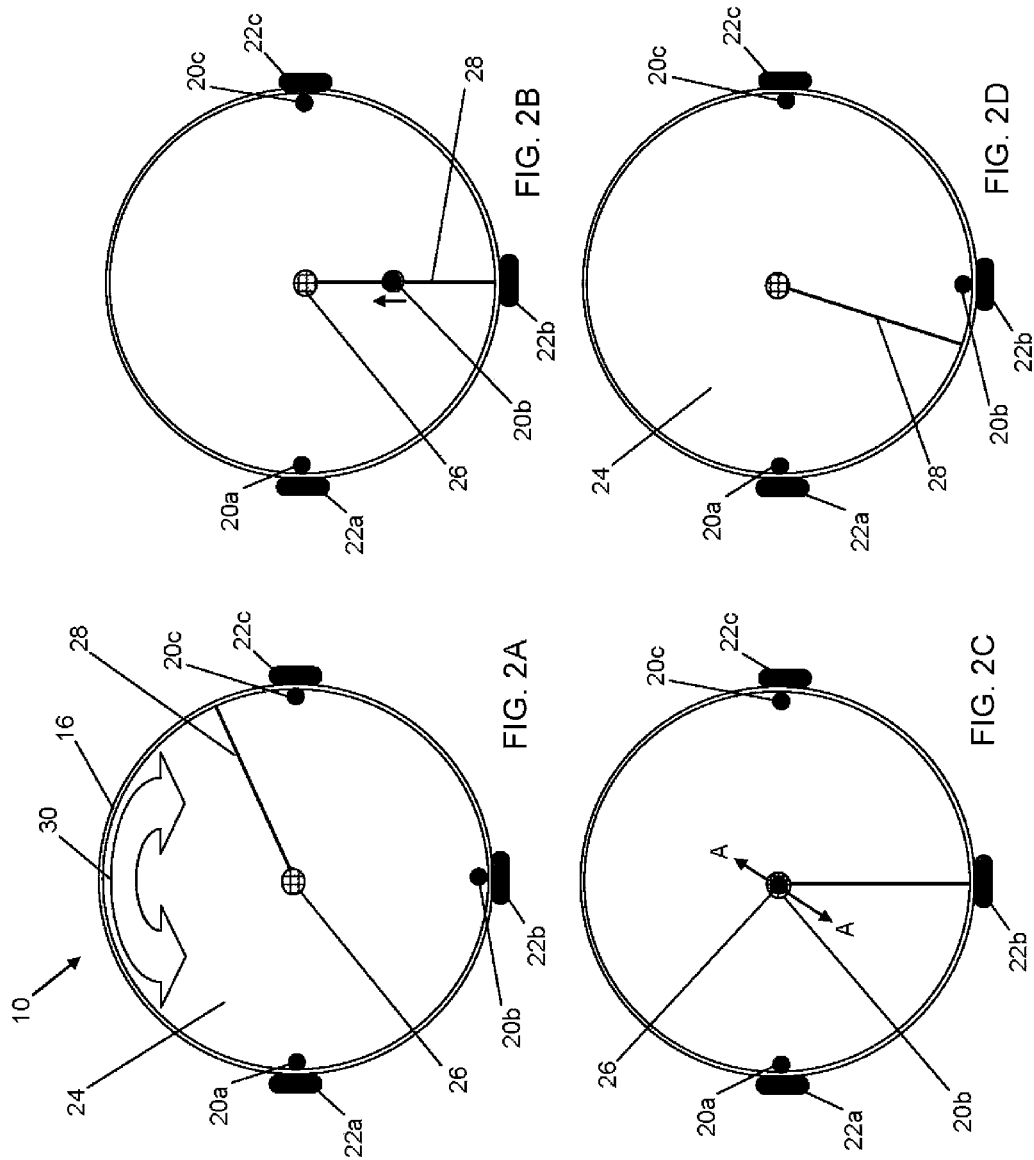
FIGS. 2A-2D are a series of cross-sectional views of the device of FIG. 1 along line 2-2 illustrating the unlocking and repositioning of a guidewire.

FIGS. 2A-2D are a series of cross-sectional views of the MGS device 10 of FIG. 1 along line 2-2 illustrating the unlocking and repositioning of the guidewire 20b. In FIG. 2A, all three of the guidewires (20a, 20b, 20c) are secured or locked to the engagement system (22a, 22b, 22c). In FIG. 2B, the rotating hub 24, which is free to rotate either clockwise or counter-clockwise as indicated by the bidirectional arrow 30, is rotated to position the slit 28 to line up with engagement 22b, and the guidewire 20b is unlocked from engagement 22b and moved inward toward the hemostatic valve seal 26 in the center of the rotating hub 24. In FIG. 2C, the guidewire 20b is now positioned within the hemostatic valve seal 26, and the guidewire is now free to move back and forth, or be twisted, along the longitudinal axis A-A of MGS device 10. In FIG. 2D, the guidewire 20b is returned to engagement 22b, and locked in place. The rotating hub 24 and corresponding slit 28 are now free to be rotated to another of the engagement 22a or 22c for using guidewires 20a or 20c, respectively.

Figure 3:
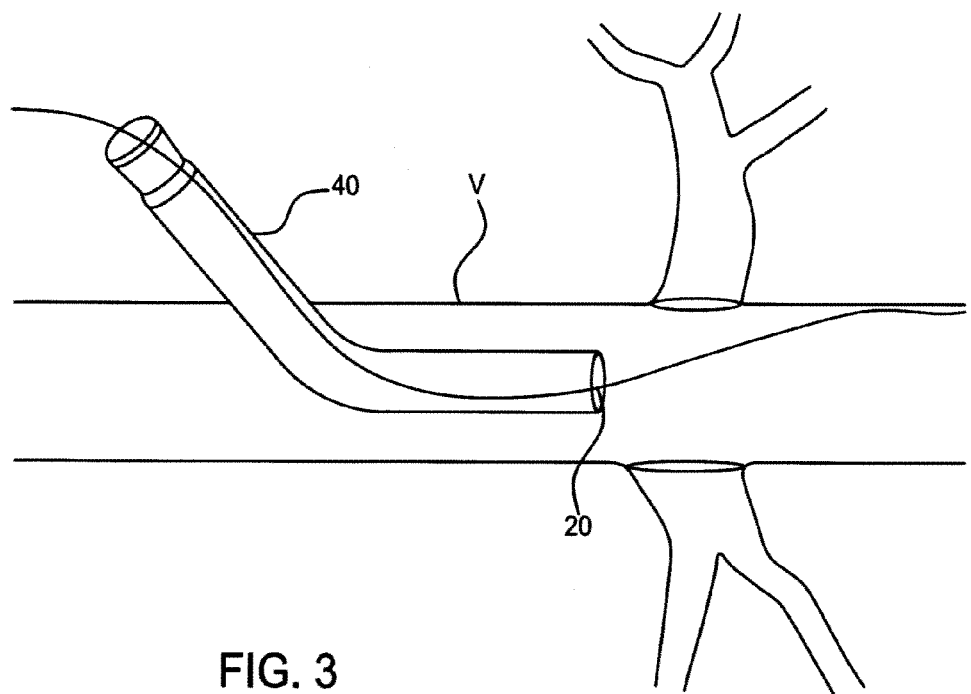
FIG. 3 is a perspective view of a conventional prior art sheath deployed in a vessel that provides single guidewire access to a vessel.

FIG. 3 is a perspective view of a conventional sheath 40 deployed in a vessel that provides single guidewire 20 access to a vessel V. As is evident from FIG. 3 only a single vessel or vascular branch is accessed for treatment with the conventional sheath 40. However, in instances where lesions or stenosis are present at a bifurcation in a patient's vessel, or a physician wants to introduce multiple interventional devices to the vessel, or the physician desires to introduce drugs to the site, separate catheters and guidewires must be inserted into branches of the bifurcation, necessitating the introduction of multiple catheters and guidewires through multiple sheaths of conventional design.

Figure 4:
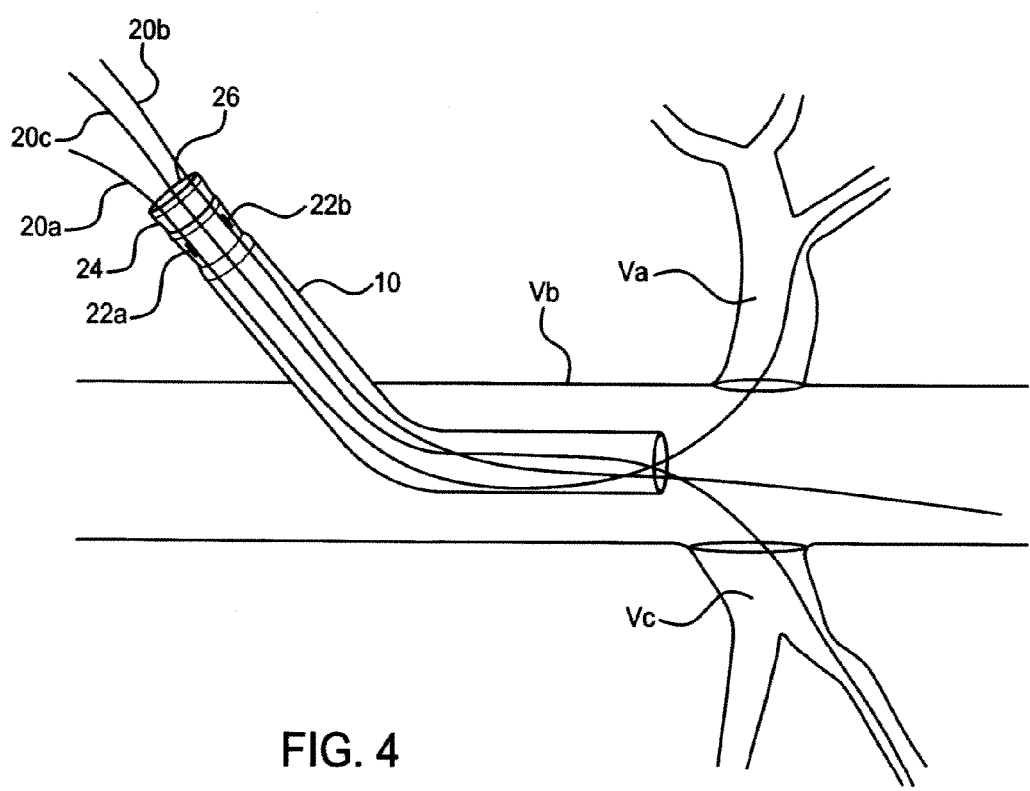
FIG. 4 is a perspective view of a deployment of the inventive MGS that illustrates simultaneous access to different arteries.

FIG. 4 is a perspective view of a vascular deployment of the inventive multi-guidewire sheath (MGS) that illustrates simultaneous access to different arteries with a single sheath inserted in a patient's body. In the deployment shown, guidewires 20A and 20B are in a locked position with engagement system 22a and 22b, respectively. Guidewire 20c is positioned in hemostatic valve seal 26 in the center of the rotating hub 24, and guidewire 20c is free to move back and forth, or be twisted within branch vessel Vc. As described above, each of the guidewires (20a, 20c, 20c) are readily moved independently to access multiple vessels with a single MGS inserted in a patient. As a result, complex procedures are made feasible with reduced anesthesia exposure to a subject.

The foregoing description is illustrative of particular embodiments of the invention, but is not meant to be a limitation upon the practice thereof. The following claims, including all equivalents thereof, are intended to define the scope of the invention.

The invention claimed is:

1. A sheath for insertion into a vessel, said sheath comprising:
   a lumen with a proximal end configured for insertion into said vessel and a distal end;
   a plurality of guidewires for simultaneous insertion within said lumen;
   an engagement system with a series of wire-lock engagement points affixed to said distal end for individually engaging each of said plurality of guidewires;
   a rotatable hub at the distal end of said sheath configured with a hemostatic valve and a slit extending from said hemostatic valve to an outer edge of said hub; and
   wherein a guidewire of said plurality of guidewires is individually adjustable when said slit is aligned with an engagement point corresponding to said guidewire, and the engagement point is unlocked to provide movement of said guidewire to said hemostatic valve via said slit.

2. The sheath of claim 1 wherein said plurality of guidewires when engaged in said series of wire-lock engagement points are prevented from being dislodged when one guidewire from one of said plurality of guidewires is being used in said sheath.

3. The sheath of claim 1 wherein said rotating hub is free to rotate either clockwise or counter-clockwise.

4. The sheath of claim 1 wherein said engagement system secures said plurality of guidewires in independent positions in multiple target arteries.

5. The sheath of claim 1 wherein said lumen has an intra-arterial portion that corresponds to French sizes.

6. The sheath of claim 1 wherein said sheath is constructed with biocompatible polyurethane materials.

7. The sheath of claim 6 wherein said biocompatible polyurethane materials are reinforced with metal or nitonal.

8. The sheath of claim 1 wherein the distal end flairs outward.

9. The sheath of claim 1 wherein the distal end is centered on a longitudinal axis.

10. The sheath of claim 9 wherein said hemostatic valve is centered on the longitudinal axis.

11. A method of using a sheath in a subject, the method comprising:
- inserting a sheath into a subject vessel, said sheath comprising a lumen with a proximal end configured for insertion into said vessel and a distal end; a plurality of guidewires for simultaneous insertion within said lumen; an engagement system with a series of wire-lock engagement points affixed to said distal end for individually engaging each of said plurality of guidewires; and a rotatable hub at the distal end of said sheath configured with a hemostatic valve and a slit extending from said hemostatic valve to an outer edge of said hub in a patient vessel;
- selecting a first guidewire from said plurality of guidewires by rotating said hub to align said slit with one of said series of wire-lock engagement points;
- disengaging said first guidewire from the one of said series of wire-lock engagement points;
- moving said first guidewire along said slit until reaching said hemostatic valve; and
- using said selected guidewire by at least one of: moving back and forth, or twisting.

12. The method of claim 11 further comprising:
- returning said first guidewire from said hemostatic valve along said slit back to said aligned wire-lock engagement point;
- reengaging said selected guidewire in said aligned wire-lock engagement; and
- selecting a second guidewire from said plurality of guidewires by repeating the steps of said selecting, said disengaging, said moving, and said using.

13. A sheath for insertion into a vessel, said sheath comprising:
- a lumen with a proximal end configured for insertion into said vessel and a distal end;
- a plurality of guidewires for simultaneous insertion within said lumen;
- an engagement system with a series of wire-lock engagement points affixed to said distal end for individually engaging each of said plurality of guidewires;
- a rotatable hub at the distal end of said sheath configured with a hemostatic valve and a slit extending from said hemostatic valve to an outer edge of said hub;
- wherein a guidewire of said plurality of guidewires is individually adjustable when said slit is aligned with an engagement point corresponding to said guidewire, and the engagement point is unlocked to provide movement of said guidewire to said hemostatic valve via said slit, wherein in the event said guidewire is positioned in said hemostatic valve, said guidewire is free to move back and forth, or be twisted, along a longitudinal axis of said sheath.

* * * * *